US007156828B2

(12) United States Patent
Ostrow

(10) Patent No.: US 7,156,828 B2
(45) Date of Patent: Jan. 2, 2007

(54) CHAFING BARRIER FOR USE IN A SANITARY UNDERGARMENT

(76) Inventor: Carol Ostrow, 641 Fifth Ave., New York, NY (US) 10022

(*) Notice: Subject to any disclaimer, the term of this patent is extended or adjusted under 35 U.S.C. 154(b) by 6 days.

(21) Appl. No.: 10/987,643

(22) Filed: Nov. 12, 2004

(65) Prior Publication Data
US 2005/0107762 A1 May 19, 2005

Related U.S. Application Data

(60) Provisional application No. 60/519,488, filed on Nov. 13, 2003.

(51) Int. Cl.
*A61F 13/15* (2006.01)
(52) U.S. Cl. .............. 604/385.04; 604/385.01; 604/385.16; 604/385.25; 604/385.28; 604/369
(58) Field of Classification Search .......... 604/385.01, 604/369, 385.04, 385.16, 385.25, 385.28, 604/401
See application file for complete search history.

(56) References Cited

U.S. PATENT DOCUMENTS 3,400,718 A * 9/1968 Saijo .................. 604/394
6,156,024 A * 12/2000 Schulte et al. ......... 604/385.28

* cited by examiner

*Primary Examiner*—Jacqueline F. Stephens
(74) *Attorney, Agent, or Firm*—Roberts Mardula & Wertheim, LLC

(57) ABSTRACT

An embodiment of the present invention provides means for extending a chafing barrier through a leg opening down the upper inner thigh of the wearer of an absorbent device. The chafing barrier comprises a layer of soft padded material, such as foam plastic, wadding, elastic gel, or a similar material. In one embodiment of the present invention, the chafing barrier is attached to a disposable pad. In another embodiment of the present invention, the chafing barrier is attached to the inside of an undergarment that surrounds or is integrated with an absorbent device. In still another embodiment of the present invention, the chafing barrier further comprises a top surface of absorbent material having a dermatological agent disposed thereon. Optionally, the dermatological agent comprises a moisturizing lotion, a drying agent, an antibiotic, a fungicide, or a topical steroid to aid in healing and/or soothing chafed skin. As will be apparent to those skilled in the art, other topical materials may be incorporated on or in the chafing barrier to promote comfort and/or healing.

20 Claims, 3 Drawing Sheets

CHAFING BARRIER FOR USE IN A SANITARY UNDERGARMENT

CROSS REFERENCE TO RELATED APPLICATIONS

This application claims priority under 35 U.S.C. § 119(e) from provisional application No. 60/519,488 filed Nov. 13, 2003. The 60/519,488 provisional application is incorporated by reference herein, in its entirety, for all purposes.

BACKGROUND

Embodiments of the present invention relate generally to sanitary undergarments suitable for use with absorbent articles such as sanitary napkins, panty liners, and incontinence pads. More specifically, the present invention provides a system and method for improving the comfort and wearability of undergarments by reducing the chafing that occurs on the upper inner thigh areas of the wearer.

There is a continuing need for absorbent articles such as sanitary napkins, panty liners, and incontinence pads. These devices are typically worn in the crotch region of underwear and are designed to absorb and retain liquid and other discharges from the human body and to prevent body and clothing soiling.

Various patents teach means for improving the absorbency of such devices, the resistance to leakage, and convenience of use.

In U.S. Pat. No. 5,725,518 issued to Coates, a reusable diaper having a fluid absorbent pad on the inner surface of a waterproof, hourglass-shaped, diaper shell is described.

U.S. Pat. No. 6,224,582 issued to Zachery describes a disposable insert for use with an adult diaper, said insert having a webbed "T" configuration and a plurality of absorbent pads or batts, one of which is positioned at the lower end of the "T" configuration such that when the insert is placed on the patient the wide portion is across the patient's abdomen and the narrow portion is positioned through the patient's crotch, fluid tending to puddle is absorbed without leakage. The insert may be applied to the patient with very little, if any, lifting of the patient required.

Other devices are described in U.S. Pat. No. 5,522,809 issued to Larsonneur, U.S. Pat. No. 4,834,737 issued to Khan, U.S. Pat. No. 6,558,364 issued to Santa Cruz, U.S. Pat. No. 6,623,466 issued to Richardson, U.S. Pat. No. 5,325,543 issued to Allen, U.S. Pat. No. 5,360,422 issued to Brownlee, et al., U.S. Pat. No. 5,725,518 issued to Coates, U.S. Pat. No. 6,491,677 issued to Glaug et al., and U.S. Pat. No. 6,423,043 issued to Gustafsson.

The above references are hereby incorporated by reference in their entirety.

Gustafsson suggests a means for reducing chafing. Gustafsson ascribes the potential for chafing to the width of an absorbent device during use. According to Gustafsson, soft components that are deformed during use do not contribute to the same extent to the width of the absorbent device during use as non-deformable components. Gustafsson also describes a stiff shell component of an absorbent device that does not deform in the transverse direction by the compressive forces that arise between the user's thighs. To reduce the risk of chafing from the edges of the stiff shell, the shell is dressed with a layer of soft, padded material, such as foam plastic, wadding or similar material.

The risk of chafing is not limited to the non-deforming component of the absorbent device. Typically, a barrier cuff surrounds the upper thighs to prevent leakage. This barrier cuff is secured by elastic or other stretchable means. As a wearer moves, the barrier cuff may slide against the skin causing abrasions. Once the skin has been irritated in this manner, the discomfort level of the wearer rises dramatically. For bedridden adults, the risk of chafing is exacerbated by the size of the absorbent device needed to effectively control discharges and the lack of mobility of the wearer. Chafing may not only occur at the barrier cuffs, but by rubbing of the upper inner thighs against each other. Padding the shell of an absorbent device does not protect against either of these sources of chafing.

A need exists for means to make absorbent devices more comfortable by reducing or eliminating the causes of chafing in the area of the upper inner thigh.

SUMMARY

An embodiment of the present invention provides means for extending a chafing barrier through a leg opening and down the upper inner thigh of the wearer of an absorbent device. The chafing barrier comprises at least one layer of soft padded material, such as foam plastic, wadding, elastic gel, or a similar material. In one embodiment of the present invention, the chafing barrier is attached to a disposable pad. In another embodiment of the present invention, the chafing barrier is attached to the inside of an undergarment that surrounds, or is integrated with, an absorbent device. In still another embodiment of the present invention, the chafing barrier further comprises a top surface of absorbent material having a dermatological agent disposed thereon. Optionally, the dermatological agent comprises a moisturizing lotion, a drying agent, an antibiotic, a fungicide, or a topical steroid to aid in healing and/or soothing chafed skin. As will be apparent to those skilled in the art, other topical materials may be incorporated on or in the chafing barrier to promote comfort and/or healing. In yet another embodiment of the present invention, the chafing barrier further comprises attaching means for securing the distal end of the chafing barrier to the upper inner thigh of the wearer.

It is an aspect of the present invention to reduce the risk of chafing in the area of the upper inner thigh of wearers of absorbent devices.

Another aspect of the present invention is to provide chafing protection while administering topical remedies for previously chafed skin or irritated skin.

Still another aspect of the present invention is to integrate a chafing barrier into an absorbent pad that can be used with absorbent undergarments.

Yet another aspect of the present invention is to integrate a chafing barrier into an undergarment that may optionally hold an absorbent pad.

These and other objects of the present invention will be more readily apparent when considered in reference to the following description and when taken in conjunction with the accompanying drawings.

In an embodiment of the present invention, a chafing barrier is used in combination with an absorbent pad suitable to be worn in the crotch region of an undergarment. The absorbent pad has a substantially elongated shape with a longitudinal direction and a transverse direction and comprises two side edges extending in the longitudinal direction. Chafing barriers are connected to opposing sides of the absorbent pad along at least a portion of each side edge. Each chafing barrier comprises at least one layer of soft padded material such as foam plastic, wadding, elastic gel, or a similar material. During use, the chafing barriers are intended be extended through leg openings of the undergarment of a user and to contact the upper inner thigh of the user to provide a barrier against chafing. In still another embodiment of the present invention, the chafing barrier further comprises a top surface of absorbent material having a dermatological agent disposed thereon. Optionally, the dermatological agent comprises a moisturizing lotion, a drying agent, an antibiotic, a fungicide, or a topical steroid to aid in healing and/or soothing chafed skin.

In another embodiment, the chafing barriers are used in combination with a sanitary undergarment. The sanitary undergarment has leg openings, each comprising an inner section circumscribing the upper inner thigh of a wearer. Chafing barriers each connect to opposing leg openings along its inner section. During use, the chafing barriers are extended through the leg openings of the undergarment of a user. The top surface of the chafing barrier shields the upper inner thigh of the user to provide a barrier against chafing.

In an exemplary embodiment of the present invention, a chafing barrier is combined with an absorbent pad suitable to be worn in the crotch region of an undergarment. The absorbent pad has a substantially elongated shape with a longitudinal direction and a transverse direction and comprises two side edges extending in the longitudinal direction. Chafing barriers each comprising a proximal end, a distal end, a top surface, and a bottom surface. The proximal ends of the chafing barriers are connected to opposing sides of the absorbent pad along at least a portion of each side edge. A chafing barrier is adapted to extend through a leg opening of the undergarment and to shield the upper inner thigh of a wearer to provide a barrier against chafing. Optionally, the top surface of the chafing barrier comprises a layer of soft padded material. By way of illustration and not as a limitation, the layer of soft padded material is selected from the group consisting of foam plastic, wadding, and elastic gel. In another embodiment of the present invention, the top surface of the chafing barrier has disposed thereon a medicinal agent. By way of illustration and not as a limitation, the medicinal agent is selected from the group consisting of an antibiotic, a fungicide, and an anti-inflammatory. The top surface of the chafing barrier is adapted to contact the upper inner thigh of the wearer. In yet another embodiment of the present invention, the chafing barrier further comprises attaching means located at the distal end and wherein the attaching means are adapted to secure the distal end of the chafing barrier to the upper inner thigh of the wearer. In an embodiment of the present invention, the attaching means are secured to the bottom surface of the chafing barrier. In yet another embodiment of the present invention, the chafing barrier is contoured to approximate the shape of the upper inner thigh.

In another exemplary embodiment of the present invention, a chafing barrier is combined with a sanitary undergarment having leg openings each comprising an inner section circumscribing an upper inner thigh region of a wearer. A chafing barrier comprising a proximal end, a distal end, a top surface, and a bottom surface and connected to a leg opening along its inner section, whereby the chafing barrier is adapted to extend through the leg opening and to shield the upper inner thigh to provide a barrier against chafing. Optionally, the top surface of the chafing barrier comprises a layer of soft padded material. By way of illustration and not as a limitation, the layer of soft padded material is selected from the group consisting of foam plastic, wadding, and elastic gel. In another embodiment of the present invention, the top surface of the chafing barrier has disposed thereon a medicinal agent. By way of illustration and not as a limitation, the medicinal agent is selected from the group consisting of an antibiotic, a fungicide, and an anti-inflammatory. The top surface of the chafing barrier is adapted to contact the upper inner thigh of the wearer. In yet another embodiment of the present invention, the chafing barrier further comprises attaching means located at the distal end and wherein the attaching means are adapted to secure the distal end of the chafing barrier to the upper inner thigh of the wearer. In an embodiment of the present invention, the attaching means are secured to the bottom surface of the chafing barrier. In yet another embodiment of the present invention, the chafing barrier is contoured to approximate the shape of the upper inner thigh.

DETAILED DESCRIPTION

An embodiment of the present invention provides means for extending a chafing barrier through a leg opening down the upper inner thigh of the wearer of an absorbent device. The chafing barrier comprises a layer of soft padded material, such as foam plastic, wadding, elastic gel, or a similar material. In one embodiment of the present invention, the chafing barrier is attached to a disposable pad. In another embodiment of the present invention, the chafing barrier is attached to the inside of an undergarment that surrounds or is integrated with an absorbent device. In still another embodiment of the present invention, the chafing barrier further comprises a top surface that is disposed to contact the skin. The top surface comprises an absorbent material having a lotion, ointment or powder disposed thereon. Optionally, the lotion, ointment or powder may further comprise an antibiotic, a fungicide, and/or an anti-inflammatory to aid in healing and/or soothing chafed or irritated skin. As will be apparent to those skilled in the art, other topical materials may be incorporated on or in the chafing barrier to promote comfort and/or healing. In yet another embodiment of the present invention, the chafing barrier further comprises attaching means for securing the end of the chafing barrier to the upper inner thigh of the wearer. In this embodiment, the attaching means are secured to the bottom surface of the chafing barrier (away from the skin) and hold the chafing barrier in place during movement by the wearer.

Figure 1:
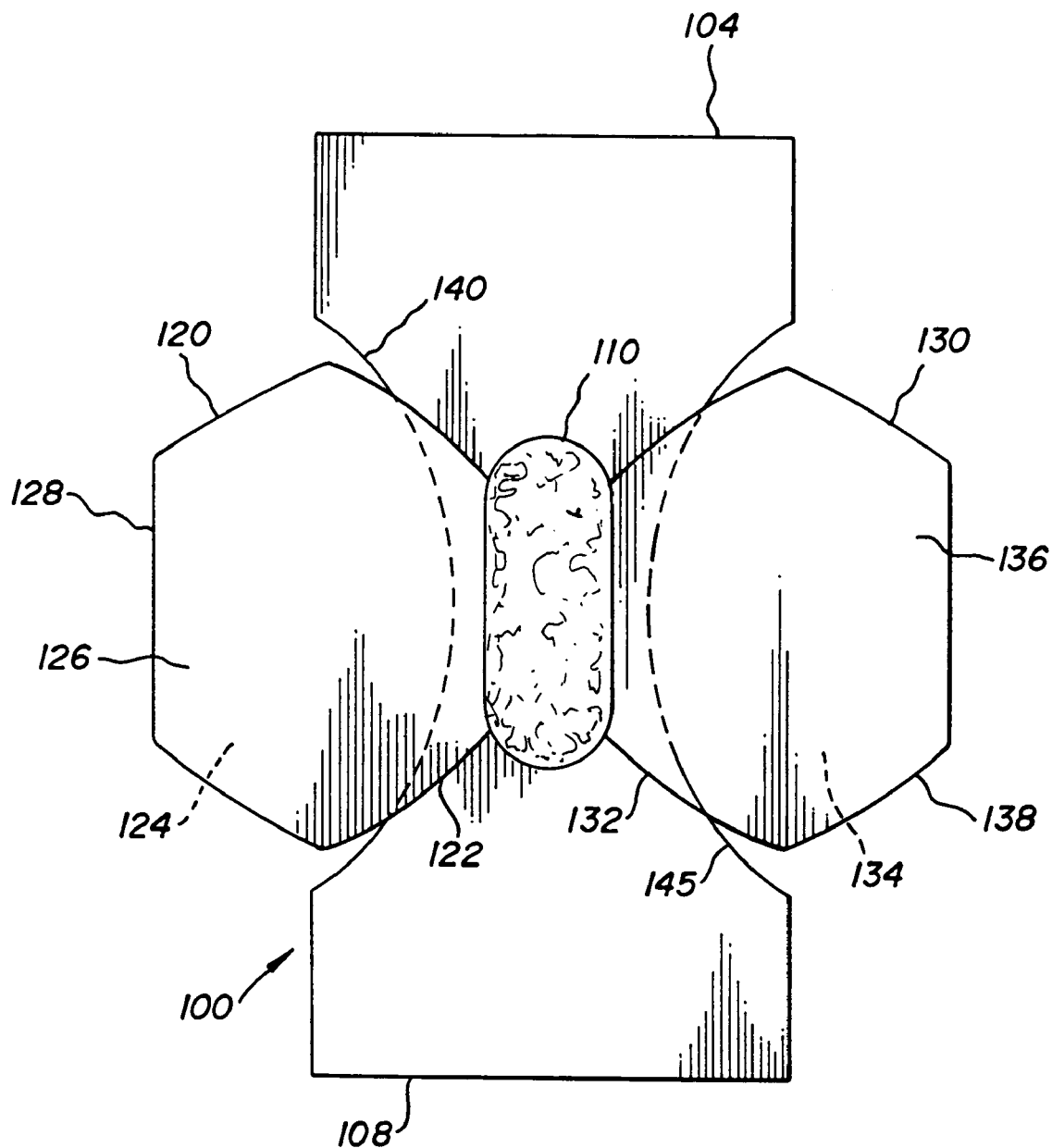
FIG. 1 illustrates a chafing barrier integrated with an absorbent pad according to embodiments of the present invention.

FIG. 1 illustrates a chafing barrier integrated with an absorbent pad according to embodiments of the present invention. Referring to FIG. 1, an undergarment 100, such as a panty, is illustrated. Undergarment 100 is depicted as a foldable device in which a top panel edge 104 and a bottom panel edge 108 are joined by suitable fasters around the waist of a wearer thereby forming leg openings 140 and 145 (see also FIG. 3, 340 and 345). However, the invention is not so limited. In an alternative embodiment of the present invention, the top and bottom panel edges (104 and 108) are sewn to form a garment in which the wearer steps through the leg opens and pulls the garment to the waist where it is secured by suitable fasteners.

Absorbent pad 110 is located in the crotch portion of undergarment 100. Optionally, absorbent pad 110 is removable and secured to undergarment 100 using adhesive means. In an alternate embodiment, absorbent pad 110 is integrated into undergarment 100. In yet another embodiment, undergarment 100 is disposable.

Attached to absorbent pad 110 is a first chafing barrier 120 and a second chafing barrier 130, each chafing barrier (120 and 130) being substantially opposed to each other. Each chafing barrier comprises a proximal end (122 and 132), a distal end (128 and 138), a top surface (126 and 136), and a bottom surface (124 and 134). In an embodiment of the present invention, at least one layer of soft padded material, such as foam plastic, wadding, elastic gel, or a similar material is disposed on top surfaces 126 and 136. First chafing barrier 120 is disposed to extend through and beyond leg opening 140. Second chafing barrier 130 is disposed to extend through and beyond leg opening 145. In an embodiment of the present invention, each chafing barrier (120 and 130) is six inches wide and extends six inches from its respective leg opening (140 and 145). However, this is not meant as a limitation. Because each wearer will have different physical attributes, other widths and lengths are possible without departing from the scope of the present invention.

The top surface 126 of first chafing barrier 120 and the top surface 136 of second chafing barrier 130 shield, and may contact, the upper inner thigh region of the wearer of undergarment 100. This contact may be enhanced by pressure from leg openings 140 and 145 created by tightening the undergarment around the waist of the wearer or by barrier cuffs (not shown) imposed on leg openings 140 and 145. In still another embodiment of the present invention, each chafing barrier (120 and 130) is shaped so as to approximate the contour of the upper inner thigh region of the wearer of the undergarment 100.

In another embodiment of the present invention, top surfaces 126 and 136 comprise absorbent material having a lotion, ointment or powder disposed thereon. Optionally, the lotion, ointment or powder may further comprise an antibiotic, a fungicide, and/or an anti-inflammatory to aid in healing and/or soothing chafed skin. As will be apparent to those skilled in the art, other topical materials may be incorporated on or in the chafing barrier to promote comfort and/or healing.

Figure 3:
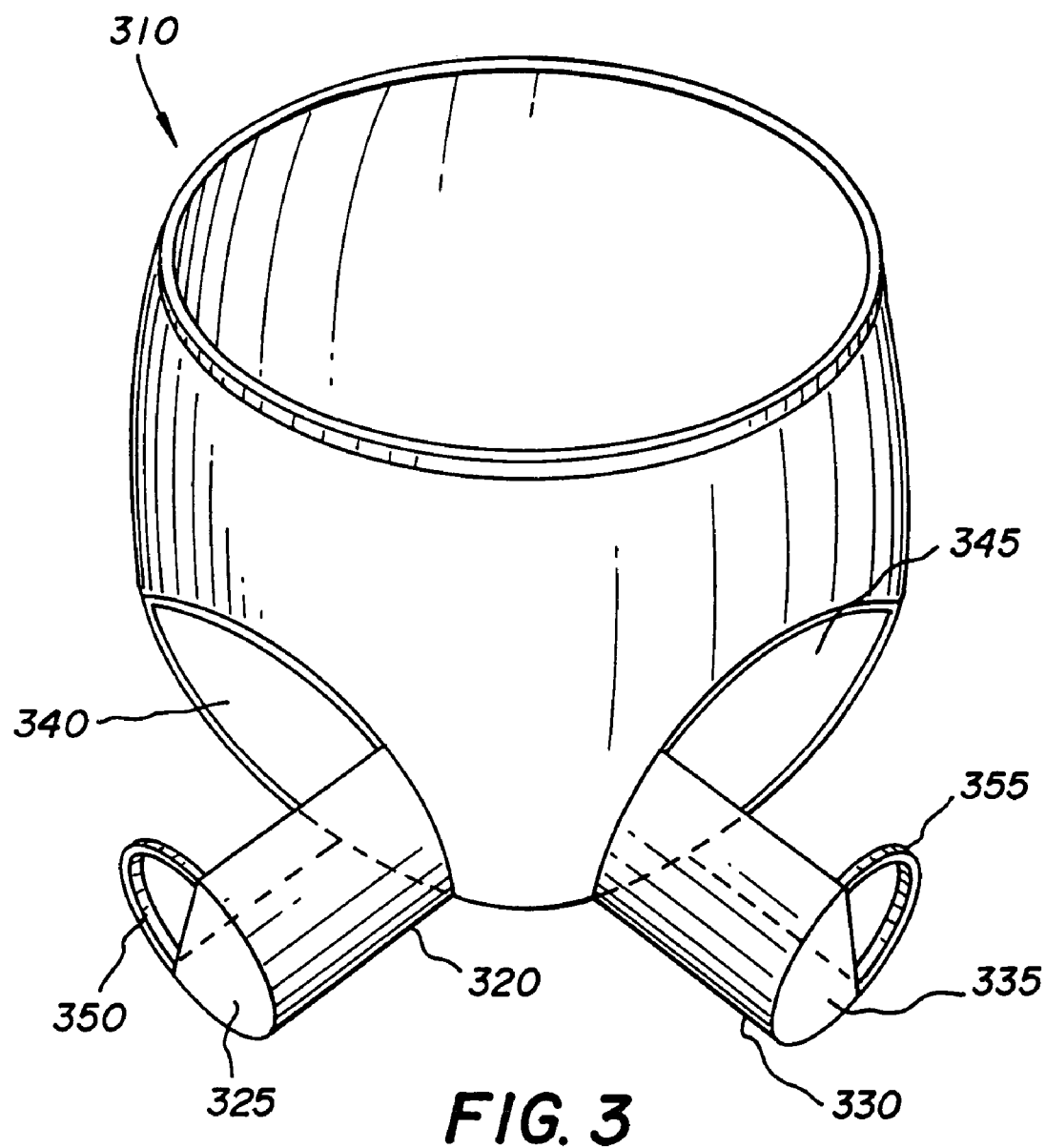
FIG. 3 illustrates an undergarment in which chafing barriers have been deployed according to embodiments of the present invention.

In yet another embodiment of the present invention, the chafing barrier further comprises attaching means for securing the distal end of the chafing barrier to the upper inner thigh of the wearer. In this embodiment, the attaching means are secured to the bottom surface of the chafing barrier (away from the skin) and hold the chafing barrier in place during movement by the wearer. Referring to FIG. 3, attaching means 350 and 355 are illustrated. In an embodiment of the present invention, attaching means 350 and 355 are formed of an elastic material and are connected to chafing barriers 320 and 330 respectively by fasteners (for example, snaps or a loop-hook mesh) known in the art.

Figure 2:
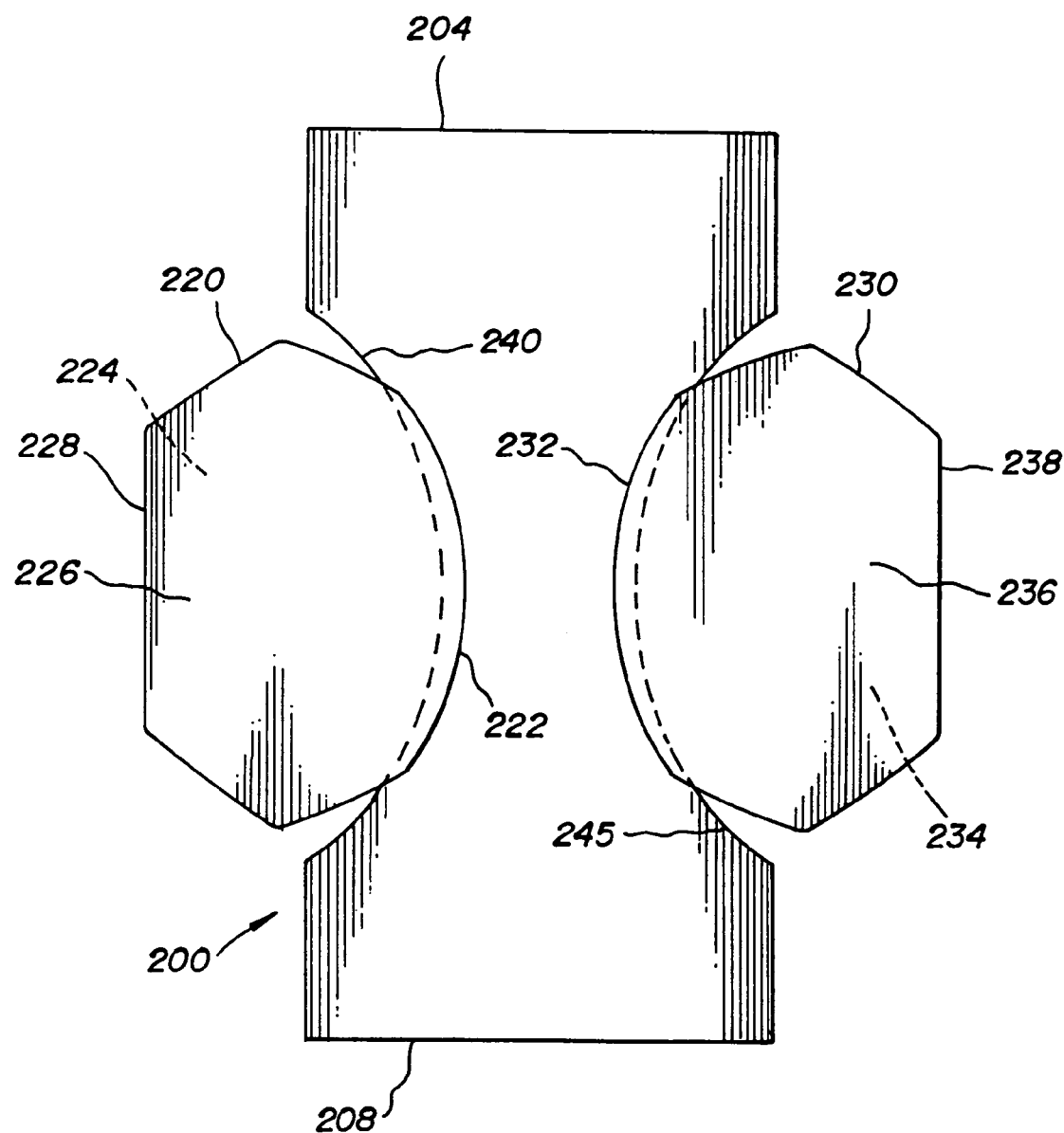
FIG. 2 illustrates a chafing barrier integrated with an undergarment according to embodiments of the present invention.

FIG. 2 illustrates a chafing barrier integrated with an undergarment according to embodiments of the present invention. Referring to FIG. 2, an undergarment 200 is illustrated. Undergarment 200 is depicted as a foldable device in which a top panel edge 204 and a bottom panel edge 208 are joined by suitable fasters around the waist of a wearer thereby forming leg openings 240 and 245. However, the invention is not so limited. In an alternative embodiment of the present invention, the top and bottom panel edges (204 and 208) are sewn to form a garment, such as a panty, in which the wearer steps through the leg openings and pulls the garment to the waist where it is secured by suitable fasteners.

Attached to undergarment 200 is a first chafing barrier 220 and a second chafing barrier 230, each chafing barrier (220 and 230) being substantially opposed to each other and attached to undergarment 100 proximal to leg openings 240 and 245 respectively.

Each chafing barrier comprises a proximal end (222 and 232), a distal end (228 and 238), a top surface (226 and 236), and a bottom surface (224 and 234). In an embodiment of the present invention, at least one layer of soft padded material, such as foam plastic, wadding, elastic gel, or a similar material is disposed on top surfaces 226 and 136.

First chafing barrier 220 is disposed to extend through and beyond leg opening 240. Second chafing barrier 230 is disposed to extend through and beyond leg opening 245.

The top surface 226 of first chafing barrier 220 and the top surface 236 of second chafing barrier 230 shield, and may contact, the upper inner thigh region of the wearer of undergarment 200. This contact may be enhanced by pressure from leg openings 240 and 245 created by tightening the undergarment around the waist of the wearer or by barrier cuffs (not shown) imposed on leg openings 240 and 245. In still another embodiment of the present invention, each chafing barrier (220 and 230) is shaped so as to approximate the contour of the upper inner thigh region of the wearer of the undergarment 200.

In another embodiment of the present invention, top surfaces 226 and 236 comprise absorbent material having a lotion, ointment or powder disposed thereon. Optionally, the lotion, ointment or powder may further comprise an antibiotic, a fungicide, and/or an anti-inflammatory to aid in healing and/or soothing chafed skin. As will be apparent to those skilled in the art, other topical materials may be incorporated on or in the chafing barrier to promote comfort and/or healing.

In yet another embodiment of the present invention, a chafing barrier further comprises attaching means for securing the distal end of the chafing barrier to the upper inner thigh of the wearer. In this embodiment, the attaching means are secured to the bottom surface of the chafing barrier (away from the skin) and hold the chafing barrier in place during movement by the wearer. Referring to FIG. 3, attaching means 350 and 355 are illustrated. In an embodiment of the present invention, attaching means 350 and 355 are formed of an elastic material and are connected to chafing barriers 320 and 330 respectively by fasteners (for example, snaps or a loop-hook mesh) known in the art.

FIG. 3 illustrates an undergarment in which chafing barriers have been deployed according to embodiments of the present invention. Extending from undergarment 310 through leg openings 340 and 345 are a first chafing barrier 320 and a second chafing barrier 330 respectively. Each chafing barrier (320 and 330) is substantially opposed to each other. The first chafing barrier 320 and second chafing barrier 330 may be attached to an absorbent pad (as described in relationship to FIG. 1) or attached to undergarment 310 (as described in relationship to FIG. 2). Optionally, the top surface of each chafing barrier (the side facing the wearer's skin) comprises at least one layer of soft padded material, such as foam plastic, wadding, elastic gel, or a similar material. In an embodiment of the present invention, each chafing barrier (320 and 330) is six inches wide and extends six inches from its respective leg opening (340 and 345). However, this is not meant as a limitation. Because each wearer will have different physical attributes, other widths and lengths are possible without departing from the scope of the present invention. In still another embodiment of the present invention, each chafing barrier (320 and 330) is shaped so as to approximate the contour of the upper inner thigh region of the wearer of the undergarment 300.

In yet another embodiment of the present invention, the chafing barrier further comprises attaching means for securing the distal end of the chafing barrier to the upper inner thigh of the wearer. In this embodiment, the attaching means are secured to the bottom surface of the chafing barrier (away from the skin) and hold the chafing barrier in place during movement by the wearer. Referring again to FIG. 3, attaching means 350 and 355 are illustrated. In an embodiment of the present invention, attaching means 350 and 355 are formed of an elastic material and are connected to chafing barriers 320 and 330 respectively by fasteners (for example, snaps or a loop-hook mesh) known in the art.

A chafing barrier for use in a sanitary undergarment has been disclosed. It will be understood by those skilled in the art that the present invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible.

What is claimed is:

1. A chafing barrier in combination with an absorbent pad comprising:
    an absorbent pad suitable to be worn in a crotch region of an undergarment, the absorbent pad having a substantially elongated shape with a longitudinal direction and a transverse direction and comprising two side edges extending in the longitudinal direction;
    attaching means located at the distal end and wherein the attaching means are adapted for securing the distal end of the chafing barrier to the inner thigh region; and
    chafing barriers each comprising a proximal end, a distal end, a top surface, and a bottom surface, wherein the proximal ends of the chafing barriers are connected to opposing sides of the absorbent pad along at least a portion of each side edge, and wherein a chafing barrier is adapted for:
        extending through a leg opening of the undergarment and covering an inner thigh region of the wearer;
        shielding the inner thigh region; and
        providing a barrier against chafing of the skin of opposing inner thigh regions.

2. The chafing barrier of claim 1, wherein the top surface of the chafing barrier comprises a layer of soft padded material.

3. The chafing barrier of claim 2, wherein the layer of soft padded material is selected from the group consisting of foam plastic, wadding, and elastic gel.

4. The chafing barrier of claim 1, wherein the top surface of the chafing barrier has disposed thereon a dermatological agent, and wherein the top surface of the chafing barrier is adapted for contacting the skin of inner thigh region.

5. The chafing barrier of claim 4 wherein the dermatological agent is selected from the group consisting of a moisturizing lotion, a drying agent, an antibiotic, a fungicide, and an anti-inflammatory.

6. The chafing barrier of claim 1, wherein the attaching means are secured to the bottom surface of the chafing barrier.

7. The chafing barrier of claim 1, wherein the chafing barrier is contoured to approximate the shape of the inner thigh region.

8. The chafing barrier of claim 1, wherein the undergarment is selected from the group consisting of a foldable diaper and a pant.

9. The chafing barrier of claim 1, wherein the attaching means comprise an elastic material and wherein the attaching means are secured to the chafing barrier via a fastener selected from the group consisting of a snap, a loop-hook mesh, and a button.

10. The chafing barrier of claim 1, wherein the top surface of the chafing barrier comprises a layer of non-absorbent material.

11. A chafing barrier in combination with a sanitary undergarment comprising:
    a sanitary undergarment having leg openings each comprising an inner section adapted for circumscribing a thigh region at the crotch of a wearer;
    a chafing barrier comprising a proximal end, a distal end, a top surface, and a bottom surface and connected to a leg opening along its inner section;
    attaching means located at the distal end, wherein the attaching means are adapted for securing the distal end of the chafing barrier to the inner thigh region;
    and wherein the chafing barrier is adapted for extending through the leg opening, for covering an inner thigh region of the wearer, and for providing a barrier against chafing of the skin of opposing inner thigh regions.

12. The chafing barrier of claim 11, wherein the top surface of the chafing barrier comprises a layer of soft padded material.

13. The chafing barrier of claim 12, wherein the soft padded material is selected from the group consisting of foam plastic, wadding, and elastic gel.

14. The chafing barrier of claim 11, wherein the top surface of the chafing barrier has disposed thereon a dermatological agent, and wherein the top surface of the chafing barrier is adapted for contacting the skin of the inner thigh region.

15. The chafing barrier of claim 14 wherein the medicinal agent is selected from the group consisting of a moisturizing lotion, a drying agent, an antibiotic, a fungicide, and an anti-inflammatory.

16. The chafing barrier of claim 11, wherein the attaching means are secured to the bottom surface of the chafing barrier.

17. The chafing barrier of claim 11, wherein the chafing barrier is contoured to approximate the shape of the inner thigh region.

18. The chafing barrier of claim 11, wherein the undergarment is selected from the group consisting of a foldable diaper and a pant.

19. The chafing barrier of claim 11, wherein the attaching means comprise an elastic material and wherein the attaching means are secured to the chafing barrier via a fastener selected from the group consisting of a snap, a loop-hook mesh, and a button.

20. The chafing barrier of claim 11, wherein the top surface of the chafing barrier comprises a layer of non-absorbent material.

* * * * *